United States Patent [19]
Miller et al.

[11] Patent Number: 6,107,067
[45] Date of Patent: Aug. 22, 2000

[54] POROUS, NON-MACROPOROUS, INORGANIC OXIDE CARRIER BODY FOR IMMOBILIZING MICROORGANISMS FOR BIOREMEDIATION

[75] Inventors: James George Miller, Ellicott City; Robert Haywood Bates, deceased, late of Baltimore, by Louise Marie Bates, legal representative; Timothy Allen Boyer, Eldersburg; Donald Richard Durham, Gaithersburg, all of Md.

[73] Assignee: W. R. Grace & Co.-Conn., New York, N.Y.

[21] Appl. No.: 09/110,582

[22] Filed: Jul. 6, 1998

[51] Int. Cl.[7] ............................. C12N 11/14; C12N 5/00; C12P 1/00; C12S 3/00

[52] U.S. Cl. ................... 435/176; 435/41; 435/262.5; 435/395; 435/403; 210/615; 210/616

[58] Field of Search .................. 435/41, 176, 262.5, 435/395, 403; 210/615, 616

[56] References Cited

U.S. PATENT DOCUMENTS

| | | | |
|---|---|---|---|
| 3,666,627 | 5/1972 | Messing | 435/176 |
| 3,953,292 | 4/1976 | Burns | 435/176 |
| 4,113,566 | 9/1978 | Hamsher et al. | 435/44 |
| 4,415,662 | 11/1983 | Thirumalachar et al. | 435/176 |
| 5,096,814 | 3/1992 | Aivasidis et al. | 435/41 |
| 5,395,808 | 3/1995 | Miller et al. | 502/7 |
| 5,443,975 | 8/1995 | Cervelli et al. | 435/175 |
| 5,614,401 | 3/1997 | Takahashi et al. | 435/176 |
| 5,618,736 | 4/1997 | Tone | 436/527 |

OTHER PUBLICATIONS

Grace Technical Bulletin 928–1, Physical and Chemical Properties of Inorganic Oxide Biocarriers.

Grace Technical Bulletin 928–2, Performance Properties of Inorganic Oxide Biocarriers—Type Z.

Grace Technical Bulletin 928–3, Performance Properties of Inorganic Oxide Biocarriers—Type CZ.

New Composite Biocarriers Engineered to Contain Adsorptive and Ion–Exchange Properties Improved Immobilized––Cell Biorector Process Dependability; Durham et al; vol. 60, No. 11, Applied and Environmental Microbiology, Nov. 1994, p. 4178–4181.

Characteristics of Inorganic Biocarriers That Moderate System Upsets During Fixed–Film Biotreatment Processes; Durham et al; vol. 60, No. 9, Applied and Environmental Microbiology, Sep. 1994, p. 3329–3335.

*Primary Examiner*—David M. Naff
*Attorney, Agent, or Firm*—Robert A. Maggio; Beverly J. Artale

[57] ABSTRACT

A porous inorganic oxide carrier body for immobilizing living cells is prepared from inorganic oxide particles such as clay particles. The particles have an average particle size of from 0.01 to 20 microns, and the carrier body has a total pore volume of 0.05 to 1.0 cc/g and an average pore diameter of 50 to 700 Å, and has substantially no pore volume in the range of 800 Å or greater. The carrier is prepared by forming a mixture containing the particles, a liquid medium and optional ingredients including zeolite and activated carbon, and forming the mixture into a shaped carrier body which may be optionally dried and calcined. Typical shapes of the carrier include spheres, cylinders, rings, honeycombs and shaped monoliths. Bacteria and other microorganisms immobilized on the carrier are useful for treatment of contaminated waste streams or contaminated vapors, or for other uses for which microorganisms are used such as the synthesis of chemicals.

28 Claims, 1 Drawing Sheet

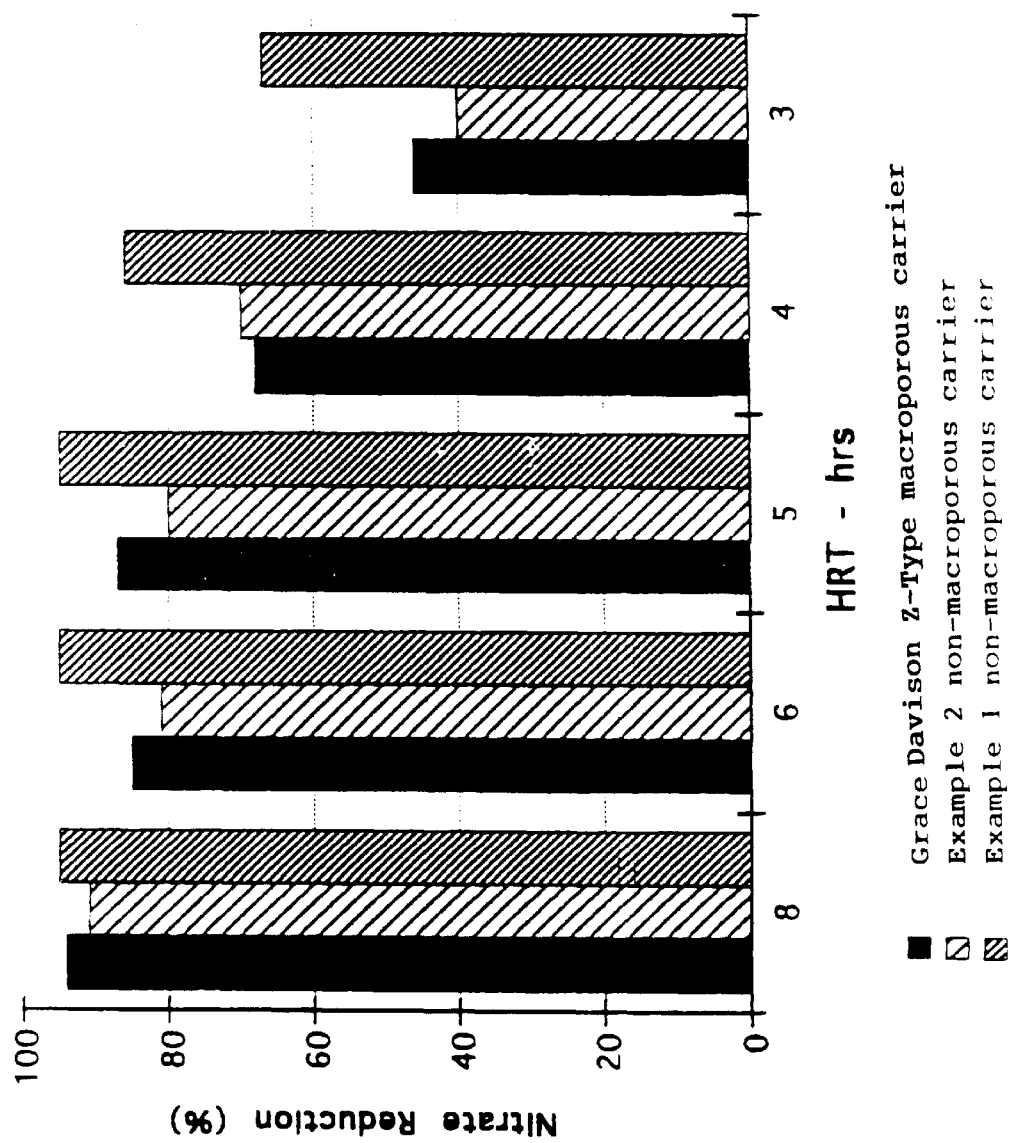

POROUS, NON-MACROPOROUS, INORGANIC OXIDE CARRIER BODY FOR IMMOBILIZING MICROORGANISMS FOR BIOREMEDIATION

FIELD OF THE INVENTION

The present invention is directed to a method for using a porous inorganic matrix as a bioreactor carrier.

More particularly, the present invention relates to a method of using a porous, inorganic oxide material having substantially no macropores as a bioreactor carrier to immobilize living cells, i.e., bacteria and other microorganisms, for catalyzation of various biochemical reactions in an industrial field, in particular, in the biotreatment of aqueous waste streams.

Further, the present invention relates to a bioreactor carrier-biocatalyst composite body having a microorganism carried on a porous inorganic oxide carrier, and a bioreactor system using such a composite body.

BACKGROUND OF THE INVENTION

Immobilized-cell bioreactor technology provides a cost-effective means for the treatment of existing environmental waste problems, such as contaminated groundwater, or for the eradication of pollutants as their point of origin. This technology generally involves the colonization of a specialized microorganism onto inorganic biocarriers as fixed films and the utilization of these colonized surfaces in controllable reaction vessels or bioreactors.

Ideally, suitable biocarriers for immobilization of microorganisms should be non-toxic and should provide a rough, irregular surface. The matrix should be hydrophilic (23) and porous (17). These properties have been shown by others to promote the adherence and proliferation of microorganisms. However, the porosity of a biocarrier has proven to be of particular importance in the immobilization of microorganisms, the leading factor of which having been found to be the degree of porosity and the size of the pore. In this connection, literature has taught that biocarriers suitable for immobilization of microorganism should contain a large fraction of macropores having a diameter equal or greater than the size of the microorganism.

DE-OS 28 39 580 discloses a number of porous carrier materials for immobilization of microorganism, 70% or more of the pores of which are at least as large as the smallest dimension of the microorganism, but smaller than 4 to 5 times the greatest dimension (in yeast cells or bacteria).

U.S. Pat. No. 5,096,814 discloses a porous inorganic carrier useful for immobilizing living cells (microorganism and animal cells) for the purification of waste water or the biotechnological production of nutritional essential or pharmacological substances. The porous carrier bodies were described as typically having an open pore volume of 35% to 85%, 20% to 80% being accounted for by macropores having a diameter of 20 to 500 $\mu$m.

U.S. Pat. No. 5,395,808 also teaches porous inorganic carrier bodies suitable for use as supports for living cells, such as bacteria. The bodies have a significantly large average pore diameter of about 0.5 to 100 micron (i.e., 5,000 to 1,000,000 Å) and a total pore volume of from about 0.1 to 1.0 cc/g.

Large pores were heretofore believed to be essential in biocarriers to adequately immobilize living cells for two reasons. First, the rate of gaseous diffusion in pore increases with increasing pore diameter. Thus, in the case where intraparticle diffusion limits the rate of catalyzed reaction, the use of a biocarrier having large pores was thought to enhance the rate of product formation.

Second, large pores in the biocarrier body allow living microorganism cells, e.g., bacteria, to be supported with the pores of the carrier body. Bacteria are typically large, with dimensions on the order of 1 $\mu$m or greater, and thus was believed not to fit in smaller pores. The presence of the bacteria in the pores was heretofore believed to be necessary to promote large bacterial populations (due to additional surface area available for colonization). The greater the concentration of bacteria, i.e., living cells, the greater the catalytic activity of the immobilized biomass. Further, bacteria in the pores of the biocarrier was believed to be required to protect the microorganism from transient upsets in the external medium because of slow rates of diffusion into the pores.

Porous inorganic carrier having large pore size suffer from various disadvantages. These include difficulty in tailing pore size to a specified range, the necessity for added burnout agents to introduce the desired porosity, poor physical integrity or dimensional stability, difficulty and costs in processing and limited shapes and sizes of the bodies. Consequently, there exists a need for porous, inorganic carriers to immobilize living cells, i.e., bacteria and other microorganism, which carriers promote comparable or greater bioactivity heretofore attributed to inorganic biocarriers having a large macropore volume, while suffering none of the disadvantages associated therewith.

Accordingly, it is an object of this invention to ameliorate or eliminate the forementioned problems by providing a carrier for immobilizing living cells which offers the advantages of ease of processing, low cost production, and good physical integrity.

It is also an object of this invention to provide a method of using a porous inorganic support as a carrier for immobilizing living cells which support contains a low pore volume in the macropore range.

It is further an object of the invention to provide a method of using a porous, non-macroporous, inorganic carrier in a bioreactor as a support for living microorganisms.

Another object of the present invention is to provide a porous, non-macroporous inorganic carrier/biocatalyst composite useful in a bioreactor system.

It is also an object of the invention to provide a bioreactor system using such carrier-biocatalyst composite.

Other facets and advantages of the present invention will be apparent from the ensuing description and the appended claims.

SUMMARY OF THE INVENTION

It has now been unexpectedly found that porous inorganic oxide materials having substantially no pore volume in the macropore range, i.e., 800 Å or greater, can be used effectively as a carrier to immobilize living cells, including bacteria and other microorganisms. The porous, non-macroporous inorganic oxide material when colonized with a desired microorganism unexpectedly exhibits a high productivity as a biocatalyst comparable to commercial support materials containing macropores large enough to inhabit the microorganism. The porous, non-macroporous inorganic oxide material offer ease of manufacture, increased physical integrity and lower product costs than typically achievable with commercial macroporous-containing supports.

The porous, non-macroporous inorganic carrier of the invention is comprised of a plurality of inorganic oxide particles and is adaptable to be resistant to acid and base upsets as well as spikes in concentration of microbial toxins.

In a preferred embodiment, the invention comprises a method of using the porous, non-macroporous inorganic oxide material as a carrier in a bioreactor in the biotreatment of aqueous waste water contaminants. Another embodiment of the invention comprises a composite body comprising the porous, non-macroporous inorganic oxide carrier and a microorganism fixed onto said carrier. A bioreactor system comprising a bioreactor vessel and the carrier-biocatalyst composite in said bioreactor vessel is also disclosed.

BRIEF DESCRIPTION OF THE DRAWING

The FIGURE shows a graphic comparison of the productivity of two porous, non-macroporous carriers of the invention with a commercial macroporous carrier to reduce nitrates using the bacteria, *Paraccocus denitrificans,* immobilized on the carriers.

DETAILED DESCRIPTION OF THE INVENTION

The porous carrier of the invention is made by preparing a mixture of inorganic oxide particles and one or more optional ingredients in a liquid medium, preferably water. The mixture is formed into the porous carrier bodies of the invention through a suitable process. Thereafter, the bodies are optionally dried and calcined.

In a preferred embodiment the porous carrier body of the invention is formed by extruding the aqueous mixture of inorganic oxide particles and any optional ingredients. The amount of the inorganic oxide particles to be used in the mixture will range from about 40 to 90%, and preferably from about 60 to 80%, of the total weight of the mixture used to form the porous carrier body prior to the addition of any optional ingredients. Inorganic oxide particles used to prepare the mixture will typically have an average particle diameter ranging from 0.01 to 20 micron. Preferably, the average particle diameter is 0.1 to 10 micron.

Other useful methods for forming bodies include pelletization, balling, and granulating, among others. After being formed, the bodies optionally may be dried and calcined. Drying will allow removal of any evaporable liquids from the bodies prior to their use, and may result in enhanced crush strength of physical integrity. Although any effective drying temperature may be used, preferred temperatures will range from room temperature to about 200° C. Suitable calcination temperatures will depend upon the function to be fulfilled by the calcination step, and the conditions to which the bodies will be subject. Suitable temperatures for complete combustion of any organic materials in the bodies after forming will typically be in the range of 400° to 700° C. For imparting greater strength to the bodies, a temperature which results in at least some sintering or vitrification of the clay and other ingredients will be necessary. Temperatures greater than about 300° C. should be suitable for this purpose.

The porous, non-macroporous carrier of the invention will have an average pore diameter of 50 to 700 Å, preferably 200 to 500 Å, although the exact choice of pore diameter will depend upon the application. The total pore volume of the biocarrier will also vary with the intended application, but will generally range from about 0.05 to 1.0 cc/g. The carrier of the invention has substantially no pore volume in the range of 800 Å or greater. That is, only 10% or less of the pores in the carrier have a pore diameter of 800 Å or greater.

The body size and shape of the porous carrier will be dictated by the circumstances of use. Typical shapes include spheres, cylinders, rings, honeycombs and shaped monoliths. Typical formed products have a diameter of at least 250 microns. Preferred combinations of size and shape are spheres or cylinders of up to 1 cm for fluidized beds; spheres, cylinders, or rings of from 1 mm to 5 cm for fixed beds; and square monoliths up to 1 m long for high space velocity applications.

In order to prevent destruction of the bodies during shipping or use, these should have reasonable mechanical strengths. For bodies with dimensions of about 3 mm, this requirement corresponds to crush strengths greater than about five pounds, as measured using a testing machine such as the Pfizer Hardness Tester Model TM141-33, manufactured by Charles Pfizer and Co., Inc., 630 Flushing Avenue, Brooklyn, N.Y. The porous bodies are placed between two parallel plates of the machine and plates are slowly brought together by hand pressure. The amount of force required to crush the particle is registered on a dial which has been calibrated in pounds force. A sufficient number (for example, 50) of particles is crushed in order to get a statistically significant estimate for the total population. The average is calculated from the individual results. Higher crush strengths may be desirable in demanding applications.

Inorganic oxide particles typically used to form the porous carriers of the invention include clay particles. By clay is meant any of the class of natural or synthetic hydrated aluminosilicates, with a general composition of $(Al_2O_3)_n (SiO_2)_m \cdot xH_2O$, although other elements also may be present. These aluminosilicates may be amorphous or crystalline in two dimension with low ion-exchange capacity. In a preferred embodiment, the clay is a natural clay such as kaolin or bentonite. The amount of clay present in the carrier body will range from 0 to 100%, preferably, 10 to 100%, and most preferably from 70 to 100%.

In one embodiment, a zeolite is added to the porous carrier. Zeolite may be added to the carrier to serve several functions. Primary among these is buffering aqueous or other liquid streams contacting the finished catalyst. Zeolites typically have high cation exchange capacities, and will contain a variety of cations (metal ions and protons) in their exchange sites at neutral pH. Upon contact with a surge of acid, the zeolite in a bed of catalyst will take up protons and release other cations, thus resisting changes in the acidity of the medium. An analogous process, e.g., exchange of sodium ions into the zeolite with release of protons on exposure to caustic, also should help to prevent excursions to high pH.

Zeolites, as taught by D. W. Breck and R. A. Anderson in Kirk-Othmer: Encyclopedia of Chemical Technology, Vol. 15, Third Edition, are crystalline aluminosilicate molecular sieves comprising elements of group IA and IIA. Chemically they are represented by the empirical formula $M_{2/n}O \cdot Al_2O_3 \cdot ySiO_2 \cdot wH_2O$ where y is 2 or greater, n is the cation valence, and w represents the water contained in the voids of the zeolite. Zeolite framework structures are made up of linked $AlO_4$ and $SiO_4$ tetrahedra which form channels or interconnecting voids that are occupied by cations and water molecules. The cations are mobile and ordinarily undergo ion exchange. Preferred zeolites for use in the present invention include, but are not limited to, Y, X, and A type zeolites, as is well known in the art. However, it is within the scope of the invention to use any zeolite.

Zeolites further may act as sorbents, and so remove undesired components from the stream contacting the catalyst. Such components could include water from a gas stream (removed through adsorption or absorption), or heavy metal ions from an aqueous stream (removed through ion exchange). Finally, the zeolites may act as catalysts, catalyzing, for example, fluid catalytic cracking or other acid-catalyzed reaction without the need for impregnation or loading with other catalyst species.

It will be recognized that as other materials may confer similar benefits to those of the zeolites, it is within the scope of this invention to use such materials. These include inorganic solids with ion exchange or sorption capabilities. For examples, zirconium phosphates are well-known for their ion exchange capacities, and so may be used here.

Zeolite is added to the carrier by addition to the inorganic oxide mixture prior to forming the carrier body. The amount of zeolite to be used may vary over a wide range, depending upon the function to be imparted, and the relative costs of the ingredients used. The amount of zeolite present in the carrier body is typically 0 to 100%, preferably, about 0.5 to 50%, most preferably and about 1 to 30%.

In another embodiment of the invention, activated carbon is added to the porous, non-macroporous carrier as an optional ingredient. Activated carbon may be added to the carrier by addition of the activated carbon to the inorganic oxide mixture along with other optional ingredients prior to forming the mixture into the carrier body. In the alternative, one or more organic compounds which may be converted to activated carbon by charring is added to the mixture, along with other optional ingredients and the mixture is formed into the desired carrier body. The carrier is then calcined to convert the organic compounds to activated carbon. The amount of activated carbon present in the porous carrier of the invention is from 0 to about 30%, preferably about 3 to 10%, of the total weight of the porous carrier.

Other optional ingredients in the mixture which are to be used to produce the porous biocarrier bodies of the invention are binders, extrusion or forming aids, burnout agents, and liquids, typically water. Binders will help to hold the bodies together and typically will include metal salts, oxides, and hydroxides, and their precursors and reaction products, the choice of which will depend upon the clay and other components present in the bodies. Preferred binders for use with kaolin-based particles are silica, silicic acid, alumina, and peptized alumina. The quantity of binders to be used will range from 0 to about 50%, and preferably from 0 to about 20%, of the total weight of the mixture used to form the porous bodies prior to the addition of any optional liquids.

Extrusion and forming aids, if used, will help to ease the process used to form the porous bodies, and may improve their green strength before calcination. Typical aids will include surfactants. A preferred extrusion aid is methyl cellulose. The quantity of optional extrusion aids to be used can range from 0 up to about 20% and preferably up to about 5%, of the total weight of the mixture used to form the porous bodies prior to the addition of any optional liquids.

Burnout agents, if used, may impart increased porosity or pores of alternate size to the porous bodies. Typical burnout agents include carbon and various natural and artificial polymers, such as starch and methyl cellulose. The quantity of the optional burnout agents to be used will range from 0 to about 20%, and preferably up to about 5%, of the total weight of the mixture used to form the porous bodies prior to the addition of any optional liquids.

Finally, a liquid medium is used to aid in forming of the bodies. It also may increase porosity by leaving voids within the bodies upon evaporation. The preferred liquid is water, although non-aqueous liquids may be useful in some circumstances. For example, in cases where the high surface tension of water leads to pore collapse on evaporation, lower surface tension organic liquids such as acetone may help to prevent a loss of porosity. The amount of optional liquid to be used will range from 0 to about 75% of the total weight of the ingredients used.

Bacteria and other microorganisms immobilized on porous nonmacroporous biocarrier will have a variety of uses. This includes the biotreatment of aqueous waste streams, and the biofiltration of gases. Other uses include bioorganic synthesis of fine and commodity chemicals, and any other use for which bacteria are suitable. The carrier-biocatalyst composite have a catalytically effective amount of microorganism immobilized on the carrier.

Examples of a suitable microorganism include bacteria from the following genera: Pseudomonas, Acinetobacter, Mycobacterium, Corynebacterium, Arthrobacterium, Bacillius, Flavorbacterium, Nocardia, Achromobacterium, Alcaligenes, Vibrio, Azotobacter, Beijerinckia, Xanthomonas, Nitrosomonas, Nitrobacter, Methylosinus, Methylococcus, *actinomycetes* and Methylobacter. Additional microorganisms include members of the fungi, yeast, algae and protozoans.

The carrier-biocatalyst composite can be used in the biotreatment of an aqueous waste stream or contaminated vapor as packing materials for bioreactors. Microorganisms with specialized metabolic capabilities can be used to colonize or adhere to the porous support and thus serve as biocatalyst for the decontamination of waste streams. The porous packing of the bioreactor increases the total surface area for high microbiological cell densities which result in chemical degradation rates much higher than those of conventional waste treatment systems. The bioreactor provides a means of controlling conditions which favor microbial degradation of target compounds. For example, parameters such as pH, oxygenation, nutrient concentrations, temperature, salinity, electron donors and co-metabolic substrates can be controlled. The bioreactor can be run under anaerobic and aerobic conditions. The waste stream can enter the base of the reactor such that the flow is upward or it can enter the top of the bioreactor and the waste stream can be directed downward. Thus, the bioreactor can function as an upflow or downflow fixed film system, or alternatively, the system can function as a fluidized bed reactor.

Nutrients and gases are introduced into the system to support the growth of the microorganisms and to thus catalyze the destruction of the contaminant. Waste streams which can be degraded by microorganisms according to the present invention include aromatics, hydrocarbons, halogenated organic compounds, phenolic compounds, alcohols, ketones, carboxylic acids, ammonia, nitrates, nitrogenous organic compounds, aldehydes, ethers, esters, organosulfur compounds, organophosphorus compounds and mixtures thereof.

When used for treating aqueous waste streams or contaminated vapors the carrier-biocatalyst of the present invention having a microbial colonization is preferably adapted to be resistant to process upsets such as acid upset, base upset, and nutrient limitation.

The Examples below are for illustrative purposes only, and do not limit the invention, or the claims appended hereto.

EXAMPLE 1

2175 g Kaolin clay (Natka Clay, Grace Davison), 290 g Bentonite clay (HP-20, American Colloid), 435 g USY zeolite (VF USY, Grace Davison) was dry mixed in a 5 gal sigma mixer. While mixing 650 g water was added and mixing was continued for 5 minutes. 7.3 g Methylcellulose (Methocel, Dow) was then added followed by 500 g more of water. Once uniform, the resultant paste was extruded in to ¼" pallets and dried over night at 100° C. The pellets were then calcined at 600° C. for 2 hours. Crush Strength=34.6 psi, Surface Area=158 m²/g, Hg Porosimetry ($V_{tot}$=0.381 cc/cc, $V_{mac}$(>1000 A)=0.008 cc/cc, Ave Pore diameter=400 A).

EXAMPLE 2

2175 g Kaolin clay (Natka Clay, Grace Davison), 290 g Bentonite clay (HP-20, American Colloid), 435 g USY zeolite (VF USY, Grace Davison) was dry mixed in a 5 gal sigma mixer. While mixing 1050 g water was added and mixture was mixed until uniform. The resultant paste was extruded into ⅜" six spoke minilith pellets (wagon wheels) and dried 8 hours at 80° C. The pellets were then calcined at 800° C. for 2 hours. Crush Strength=17.3 psi (along spoke), Surface Area=129 m²/g, Hg Porosimetry ($V_{tot}$= 0.414 cc/cc, $V_{mac}$(>1000 A)=0.016 cc/cc, Ave Pore diameter=400 A).

EXAMPLE 3

2175 g Kaolin clay (Natka Clay, Grace Davison), 290 g Bentonite clay (HP-20, American Colloid), 435 g USY zeolite (VF USY, Grace Davison) was dry mixed in a 5 gal sigma mixer. While mixing 1150 g water was added and mixture was continued for 20 minutes. 134.3 g activated carbon, (8–30 mesh, Calgon) was then added followed by 50 g more of water. Once uniform, the resultant paste was extruded into ¼" and dried 6 hours at 80° C. The pellets were then calcined at 350° C. for 1 hour. Crush Strength=16.32 psi, Surface Area=186 m /g, Hg Porosimetry ($V_{tot}$=0.442 cc/cc, $V_{mac}$(>1000 A)=0.031 cc/cc, Ave Pore diameter=350 A).

EXAMPLE 4

Lab bioreactor studies were performed on non-macropore material described in Examples 1 and 2 (pellets and miniliths). These materials were compared against a commercial Grace Davison Type Z macroporous carrier as described in U.S. Pat. No. 5,403,799, Example 1 ($V_{tot}$=0.519 cc/cC, $V_{mac}$(>1000 A)=0.315 cc/cc) for dentrification of an aqueous waste stream. All three supports were inoculated from the same bacteria source to immobilize Paraccocus denitrificans on the surface of the supports. The graph of the FIGURE shows nitrate reduction verses hydraulic residence time (HRT) for the three supports. The two non-macroporous supports in accordance with the invention showed equal or better productivity for the reduction of nitrates as compared to the commercial macroporous support.

In the claims:

1. A porous inorganic oxide carrier body comprising a plurality of inorganic oxide particles having an average particle size of from 0.01 to 20 microns, the carrier body having a total pore volume of 0.05 to 1.0 cc/g , having an average pore diameter of 50 to 700 Å and having substantially no pore volume in the range of 800 Å or greater.

2. The carrier body of claim 1 wherein the inorganic oxide particles comprise clay.

3. The carrier body of claim 2, wherein the clay is composed of hydrated aluminosilicates.

4. The carrier body of claim 3 wherein the clay content of the carrier ranges from about 10 to 100%.

5. The carrier body of claim 2 wherein inorganic oxide particles further comprise zeolite.

6. The carrier body of claim 5 wherein zeolite is present in the amount of about 0.5 to 50% of the total weight of the carrier.

7. The carrier body of claim 2 wherein the inorganic oxide particles further comprise activated carbon.

8. The carrier body of claim 7 wherein the activated carbon is present in the amount of from about 3 to 10% of the total weight of the carrier.

9. The carrier body of claim 5 wherein the inorganic oxide particles further comprise activated carbon.

10. The carrier body of claim 9 wherein the activated carbon is present in the amount of from about 3 to 10% of the total weight of the carrier.

11. The carrier body of claim 1 wherein the inorganic oxide particles comprise zeolite.

12. The carrier body of claim 1 wherein the carrier is in a form selected from the group consisting of spheres, cylinders, rings, honeycombs, and shaped monoliths.

13. The carrier body of claim 1 wherein the carrier body further comprises a catalytically effective amount of living cells immobilized on the carrier body.

14. The carrier body of claim 13 wherein the living cells are microorganisms selected from the group consisting of bacteria, yeast, fungi, algae and protozoa.

15. The carrier body of claim 14 wherein the microorganism is bacteria.

16. The carrier body of claim 15 wherein the bacteria is selected from the group consisting of Pseudomonas, Acinetobacter, Mycobacterium, Corynebacterium, Arthrobacterium, Bacillius, Flavorbacterium, Nocardia, Achromobacterium, Alcaligenes, Vibrio, Azotobacter, Beijerinckia, Xanthomonas, Nitrosomonas, Nitrobacter, Methylosinus, Methylococcus, Methylobacter and *actinomycetes*.

17. A method for the biotreatment of a contaminated waste stream or contaminated vapor comprising contacting a waste stream or vapor comprising a chemical contaminant with the porous carrier body of claim 1, said porous carrier body having immobilized on the surface thereof a catalytically effective amount of living cells of a microorganism having the metabolic ability to catalyze the degradation of the contaminant.

18. A method for preparing a porous inorganic oxide carrier useful for immobilizing living cells, said method comprising (i) preparing a mixture of inorganic oxide particles having an average particle diameter of 0.01 to 20 microns in a liquid medium and forming the mixture into a shaped body having a total pore volume of 0.05 to 1.0 cc/g and an average pore diameter of 50 to 700 Å and having substantially no pore volume in the range of 800 Å or greater.

19. The method of claim 18 wherein the inorganic oxide particles comprise clay.

20. The method of claim 19, wherein the clay is composed of hydrated aluminosilicates.

21. The method of claim 19 wherein the inorganic oxide particles further comprise zeolite.

22. The method of claim 21 wherein zeolite is present in the amount of about 0.5 to 50% of the total weight of the carrier.

23. The method of claim 19 wherein the inorganic oxide particles further comprise activated carbon.

24. The method of claim 23 wherein the activated carbon is present in the amount of from about 3 to 10% of the total weight of the carrier.

25. The method of claim 21 wherein the inorganic oxide particles further comprise activated carbon.

26. The method of claim 25 wherein the activated carbon is present in the amount of from about 3 to 10% of the total weight of the carrier.

27. The method of claim 18 wherein the inorganic oxide particles comprise a zeolite.

28. The method of claim 18 wherein the carrier is in a form selected from the group consisting of spheres, cylinders, rings, honeycombs, and shaped monoliths.

* * * * *